United States Patent
Molinari et al.

(10) Patent No.: US 12,343,463 B2
(45) Date of Patent: Jul. 1, 2025

(54) BLOOD FILTERING MACHINE PROVIDED WITH A MEASURING SYSTEM COMPRISING OPTICAL SENSORS

(71) Applicant: MEDICA S.P.A., Medolla (IT)

(72) Inventors: Riccardo Molinari, Medolla (IT); Davide Bagnoli, Medolla (IT)

(73) Assignee: MEDICA S.P.A., Medolla (IT)

(*) Notice: Subject to any disclaimer, the term of this patent is extended or adjusted under 35 U.S.C. 154(b) by 462 days.

(21) Appl. No.: 17/916,291

(22) PCT Filed: Mar. 31, 2021

(86) PCT No.: PCT/IB2021/052683
§ 371 (c)(1),
(2) Date: Sep. 30, 2022

(87) PCT Pub. No.: WO2021/198945
PCT Pub. Date: Oct. 7, 2021

(65) Prior Publication Data
US 2023/0173152 A1    Jun. 8, 2023

(30) Foreign Application Priority Data
Mar. 31, 2020    (IT) .................. 102020000006706

(51) Int. Cl.
*A61M 1/16*    (2006.01)
*A61B 5/00*    (2006.01)
(Continued)

(52) U.S. Cl.
CPC ......... *A61M 1/1605* (2014.02); *A61B 5/1455* (2013.01); *A61B 5/6866* (2013.01);
(Continued)

(58) Field of Classification Search
CPC . A61B 5/02028; A61B 5/1455; A61B 5/6866; A61B 5/7264; A61M 1/1605;
(Continued)

(56) References Cited

U.S. PATENT DOCUMENTS

2002/0014462 A1    2/2002 Muller
2004/0254431 A1    12/2004 Necola Shehada
(Continued)

FOREIGN PATENT DOCUMENTS

EP    3553498 A1    10/2019
EP    3566729 A1    11/2019
(Continued)

OTHER PUBLICATIONS

International Search Report and Written Opinion for Corresponding Internation Application No. PCT/IB2021/052683 mailed Aug. 10, 2021.

*Primary Examiner* — Dirk R Bass
(74) *Attorney, Agent, or Firm* — MARSHALL, GERSTEIN & BORUN LLP

(57) ABSTRACT

A blood filtering machine having a blood circuit, which has a plurality of ducts made of a transparent material, and a measuring system, which has a plurality of optical sensors coupled to respective ducts. Each optical sensor has a reading window placed in a point of the respective duct, a light emitter and a light receiver. The measuring system comprises one single spectrometer, an optical mixer comprising a plurality of inputs, each connected to the light receiver of a respective one of the optical sensors, and an output, which is connected to an input of the spectrometer, and a control unit is configured to activate the light emitter of one optical sensor at a time so as to measure a parameter of one organic fluid at a time.

14 Claims, 3 Drawing Sheets

(51) Int. Cl.
  *A61B 5/1455* (2006.01)
  *A61M 1/34* (2006.01)
  *A61M 1/36* (2006.01)

(52) U.S. Cl.
  CPC ......... *A61B 5/7264* (2013.01); *A61M 1/3482* (2014.02); *A61M 1/3609* (2014.02)

(58) Field of Classification Search
  CPC .............. A61M 1/3482; A61M 1/3609; A61M 1/3646; A61M 1/3692; A61M 2205/3313; G01N 21/31; G01N 21/85; G01N 2201/084; G01N 2201/1296
  See application file for complete search history.

(56) References Cited

U.S. PATENT DOCUMENTS

| | | |
|---|---|---|
| 2009/0191105 A1 | 7/2009 | Tanahashi et al. |
| 2012/0062869 A1 | 3/2012 | Bado et al. |
| 2019/0167889 A1 | 6/2019 | Mitschulat et al. |

FOREIGN PATENT DOCUMENTS

| | | |
|---|---|---|
| JP | 2001054571 A | 2/2001 |
| WO | WO-2014161771 A1 | 10/2014 |
| WO | WO-2019/180068 A1 | 9/2019 |

BLOOD FILTERING MACHINE PROVIDED WITH A MEASURING SYSTEM COMPRISING OPTICAL SENSORS

CROSS-REFERENCE TO RELATED APPLICATIONS

This patent application is a U.S. national phase of International Patent Application No. PCT/IB2021/052683 filed Mar. 31, 2021, which claims the benefit of priority from Italian patent application no. 102020000006706 filed on Mar. 31, 2020, the respective disclosures of which are each incorporated herein by reference in their entireties.

TECHNICAL FIELD

The present invention relates to a blood filtering machine provided with a measuring system comprising a plurality of optical sensors.

STATE OF THE ART

As is known, blood filtering machines generally comprise a blood circuit, which is provided with a filter on the blood circuit, the purpose of which depends on the type of treatment to be applied to the patient, and with a possible second filter on the plasma circuit, in the case of apheresis treatments, the purpose of which is to remove specific molecules from the plasma.

Most optical sensors on the market for measuring intrinsic parameters of organic fluids operate based on specific wavelengths characteristic of the parameter intended to be measured. For example, hematocrit measuring sensors operate in the specific absorption frequencies of haemoglobin, water and a reference. Light sources of this type of optical sensors are narrow-band light emitters, which emit light within a narrow band of frequencies, as a function of the physical parameter of the organic fluid intended to be measured. This type of sensor also has a light receiver, which measures the light intensity at the different specific frequencies of the light refracted by the test organic fluid.

This type of optical sensor has some disadvantages.

First of all, the aforementioned optical sensors are highly sensitive to variations in some operating parameters of the measuring system such as, for example, the intensity of the light emitted by the light source, the opacification of the reading window, or the temperature, which result in a deterioration of the reproducibility of the measurement. Accordingly, in order to obtain the required reproducibility of the measurement, a measuring system including such optical sensors becomes complex and expensive. Furthermore, the aforementioned optical sensors do not allow the creation of a flexible measuring system, as the narrow-band light emitters must operate at specific frequencies associated with each parameter to be measured such as, for example, pH, saturation, quantity of platelets, haemoglobin concentration in the solution, or hematocrit. In other words, if it is necessary to measure several physical parameters of an organic fluid, the measuring system must include different optical sensors, that is, several optical sensors designed to operate at different wavelengths.

These disadvantages have limited the use of this type of optical sensors on blood filtering machines.

As is known, during some types of blood filtering treatments such as, for example, the Continuous Renal Replacement Therapy (CRRT), the patient undergoes a loss in weight, which must be measured with extreme accuracy in order to prevent significant side effects such as, for example, collapse or cramping.

Some known systems/apparatuses for weight loss measurement mounted in blood filtering machines have the drawback of having overall dimensions and production costs which have a significant impact on the overall dimensions and overall cost of the blood filtering machine. This problem is particularly evident in a specific category of blood filtering machines, namely dialysis machines, which cannot use scales to measure weight loss as the dialysis fluid comes from a centralized hospital system.

Some solutions for measuring patient weight loss in dialysis machines are based on volumetric systems or differential flow meters. However, no dialysis machine on the market is equipped with an auxiliary and independent system to repeat the measurement of the patient's weight loss during treatment, thereby ensuring greater safety for the patient himself/herself, as the measurement is redundant and any malfunctions of the main measuring system, which would put the patient's life at risk, especially in the case of the most vulnerable subjects, could be readily identified.

OBJECT OF THE INVENTION

The object of the present invention is to provide a blood filtering machine which is capable of reproducibly measuring multiple intrinsic parameters of the organic fluids in the blood circuit, and at the same time is easy and inexpensive to manufacture.

In accordance with the present invention, a blood filtering machine is provided as defined in the appended claims.

BRIEF DESCRIPTION OF THE DRAWINGS

The present invention will now be described with reference to the accompanying drawings, which illustrate a non-limiting embodiment thereof, wherein.

PREFERRED EMBODIMENT OF THE INVENTION

Figure 1:
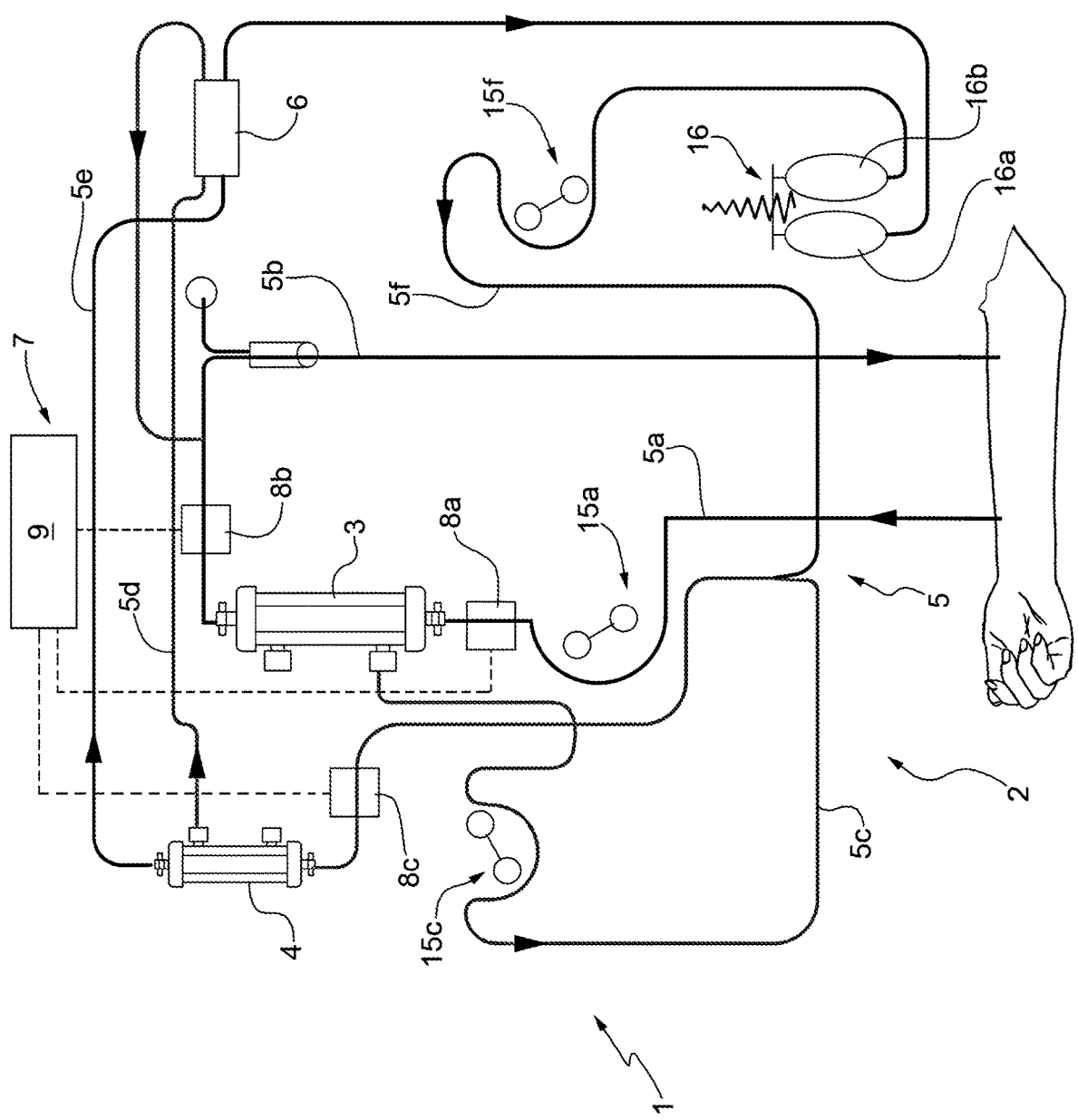
FIG. 1 schematically illustrates a blood filtering machine of the type suitable for carrying out an apheresis treatment.
Figure 2:
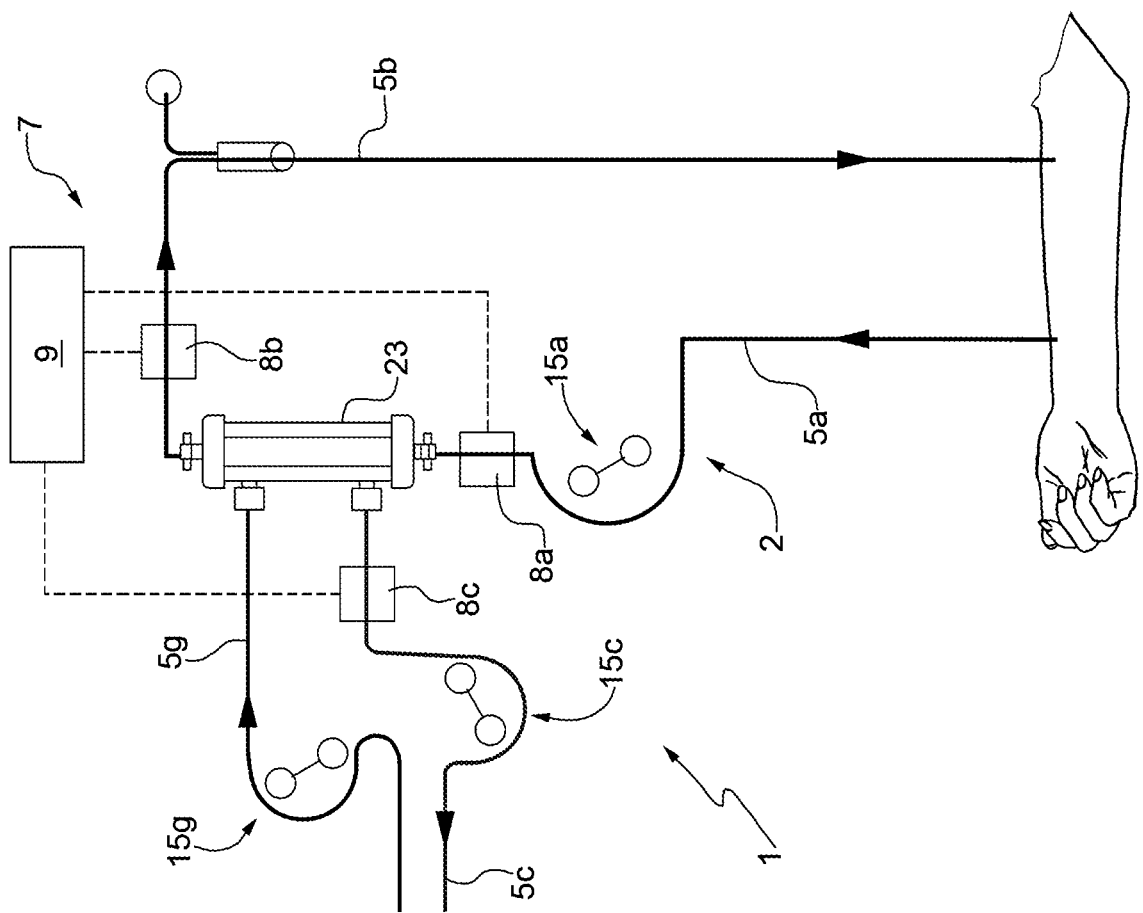
FIG. 2 schematically illustrates a blood filtering machine of the type suitable for carrying out a hemodialysis treatment.

In FIGS. 1 and 2, the numeral 1 generally indicates a blood filtering machine. The machine 1 comprises a blood circuit 2, which comprises at least one filter, the nature of which depends on the type of treatment to be carried out on the patient, and a plurality of ducts 5, which are made of a transparent material and designed to be flown through by respective fluids.

With reference to FIG. 1, the blood circuit 2 is configured to perform an apheresis treatment and comprises a plasmafilter 3, a fractionator filter 4, a selector clamp 6, and a washing apparatus 16 connected to each other through the plurality of ducts 5. The blood circuit 2 comprises a plurality of pumps, generally indicated with 15 and preferably consisting of respective peristaltic pumps, to sustain the flow of fluids inside some of the ducts 5.

The plasmafilter 3 has the task of filtering the blood taken from the patient in order to separate the corpuscular part of the blood, consisting of red blood cells, white blood cells and platelets, from the liquid part of the blood, formed by the plasma. The corpuscular part of the blood is returned to the patient, whereas the plasma is fed to the fractionator filter 4. For this purpose, the plurality of ducts 5 comprises a duct 5*a* for conveying the blood taken from the patient to the plasmafilter 3, a duct 5*b* for conveying the corpuscular part of the blood from a first output of the plasmafilter 3 to the patient, and a duct 5*c* for conveying the plasma from a second output of the plasmafilter 3 to the fractionator filter 4. The said first output of the plasmafilter 3 is preferably arranged at an upper end of the plasmafilter 3.

The fractionator filter 4 has the task of filtering the plasma in order to separate the high molecular weight part, i.e., the part of the plasma comprising cholesterol (LDL), immunoglobulin and cryoglobulin, which is retained inside the fractionator filter 4, from the low molecular weight part (the ultrafiltrate), i.e., the part of the plasma comprising albumin, IgG and HDL, which must be returned to the patient.

The high molecular weight part of the plasma will then be discarded with a special fractionator filter washing step. For this purpose, the plurality of ducts 5 comprises a duct 5*d* for conveying the plasma (the ultrafiltrate) from a first output of the fractionator filter 4 to the duct 5*b*, through the selector clamp 6, so as to return this plasma to the patient, and a duct 5*e* for connecting a second output of the fractionator filter 4 to the washing apparatus 16, through the selector clamp 6, so that the fractionator filter 4 can be washed. The duct 5*d* is joined to the duct 5*b* downstream of the selector clamp 6 by means of a bifurcation.

The selector clamp 6 has the task of selecting the opening of the duct 5*d* alone, or alternatively of the duct 5*e* alone, depending on whether the machine 1 is in a filtering step or in a fractionator filter 4 washing step, respectively. In other words, during the filtering step, the selector clamp 6 is set to open the duct 5*d* and close the duct 5*e*, so that the plasma coming out of the fractionator filter 4 can return to the patient along the ducts 5*d* and 5*b*, whereas during the washing step, the selector clamp 6 is set to open the duct 5*e* and close the duct 5*d*, so that a washing solution which has passed through the fractionator filter 4, and which is therefore rich in the high molecular weight part of the plasma, can be collected by the washing apparatus 16.

In particular, the washing apparatus 16 comprises a first sac 16*a* for containing a clean washing solution and a second sac 16*b* for collecting a "dirty" washing solution, i.e., rich in the high molecular weight part of the plasma, coming from the fractionator filter 4 through the duct 5*e*. The plurality of ducts 5 comprises a further duct 5*f* for conveying the clean washing solution from the washing apparatus 16 towards the fractionator filter 4 through the duct 5*c*. In other words, the duct 5*f* joins the duct 5*c* by means of a bifurcation.

The plurality of pumps 15 comprises a pump 15*a* preferably arranged in the area of the duct 5*a*, a pump 5*c* preferably arranged in the area of the duct 5*c*, and a pump 15*f* preferably arranged in the area of the duct 5*f*.

During the filtering step, the machine 1 is connected to the patient, and the pumps 15*a* and 15*c* are switched on to push the blood drawn along the duct 5*a* towards the plasmafilter 3 and to push the plasma along the duct 5*c* towards the fractionator filter 4, respectively, while the pump 15*f* is off, and therefore nothing flows in the ducts 5*e* and 5*f*.

During the washing step, the machine is not connected to the patient and the pumps 15*a* and 15*c* are off, and therefore nothing flows in the ducts 5*a*-5*c*, whereas the pump 5*f* is on to take the washing solution from the sac 16*a* and push it towards the fractionator filter 4 through the ducts 5*f* and 5*c*.

The washing solution passes through the fractionator filter 4, thus removing the high molecular weight part of the plasma, and the dirty washing solution comes out of the fractionator filter 4 and is collected by the sac 16*b* after passing through the duct 5*f*.

With reference to FIG. 2, the blood circuit 2 is configured to perform a hemodialysis treatment and comprises a dialyzer filter 23. For example, the dialyzer filter 23 is of the type comprising two compartments, which are mutually separated by a semi-permeable membrane and through which a flow of the blood to be treated and a flow of a dialysis fluid, otherwise known as the dialysate, flow respectively, such two flows having opposite directions. The blood impurities go into the dialysate through the semi-permeable membrane according to a mechanism known per se and therefore not described in detail herein.

The plurality of ducts 5 comprises a duct 5*a* for conveying the blood taken from the patient towards a first input of the dialyzer filter 23, a duct 5*b* for conveying the treated blood from a first output of the dialyzer filter 23 to the patient, a duct 5*g* for conveying a clean dialysate towards a second input of the dialyzer filter 23, and a duct 5*c* for extracting the "dirty" dialysate, i.e., rich in the impurities extracted from the blood, from a second output of the dialyzer filter 23.

The plurality of pumps 15 comprises a pump 15*a* preferably arranged in the area of the duct 5*a*, a pump 15*c* preferably arranged in the area of the duct 5*c*, and a pump 15*g* preferably arranged in the area of the duct 5*g*.

With reference to FIGS. 1 and 2, the machine 1 comprises a measuring system 7 designed to measure one or more intrinsic parameters of organic fluids in several points of the blood circuit 2, for example, haemoglobin, hematocrit or the quantity of blood platelets in the blood circuit 2.

The measuring system 7 comprises a plurality of optical sensors, and in particular three optical sensors indicated with 8*a*, 8*b* and 8*c*, which are arranged in different points of the blood circuit 2, and an acquisition system 9, which is connected to the optical sensors 8*a*-8*c* for acquiring and processing the signals provided by the optical sensors 8*a*-8*c*, so as to provide a measurement of at least one parameter of at least one organic fluid in the blood circuit 2.

With reference to the embodiment in FIG. 1, the optical sensor 8*a* is preferably arranged upstream of the plasmafilter 3 relative to the blood flow direction, i.e., in a point of the duct 5*a*. The optical sensor 8*b* is preferably arranged downstream of the plasmafilter 3 relative to the blood flow direction, i.e., in a point of the duct 5*b*. The optical sensor 8*c* is preferably arranged upstream of the fractionator filter 4 relative to the plasma flow direction, i.e., in a point of the duct 5*c*.

With reference to the embodiment in FIG. 2, the optical sensor 8*a* is preferably arranged upstream of the dialyzer filter 23 relative to the blood flow direction, i.e., in a point of the duct 5*a*.

The optical sensor 8*b* is preferably arranged downstream of the dialyzer filter 103 relative to the blood flow direction, i.e., in a point of the duct 5*b*.

The sensor 8*c* is preferably arranged in a point of the duct 5*c*.

Figure 3:
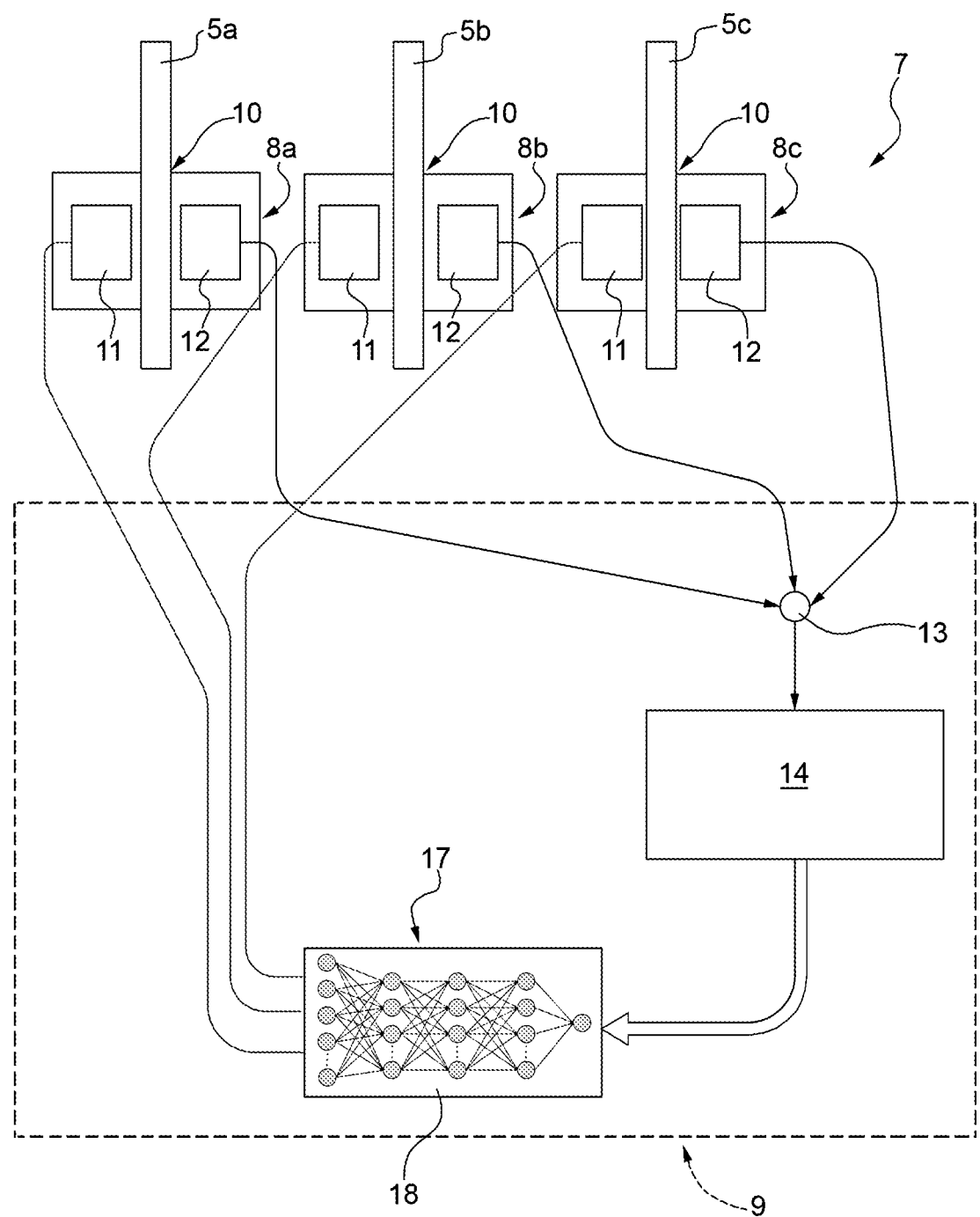
FIG. 3 schematically illustrates a measuring system for the machine in FIG. 1 or FIG. 2, comprising a plurality of optical sensors.

With reference to FIG. 3, each optical sensor 8*a*, 8*b*, 8*c* comprises a reading window 10, which is arranged in a point of the respective duct 5*a*, 5*b*, 5*c* of the blood circuit 2, and in particular wraps at least one portion of the duct 5*a*, 5*b*, 5*c*, so as to allow for the vision of the organic fluid flowing in the duct 5*a*, 5*b* and 5*c*, a light emitter 11 designed to emit light towards the duct 5*a*, 5*b*, 5*c* through the reading window 10, and a light receiver 12 designed to receive, again through the reading window 10, the light that has been emitted by the light emitter 11 and has passed through the duct 5a, 5b and 5c.

Preferably, the light emitter 11 is of the LED type.

The acquisition system 9 comprises a single spectrometer 14 connected to the light receivers 12 of the optical sensors 8a, 8b and 8c by means of an optical mixer 13, and a control unit 17 which drives the light emitters 11 of the optical sensors 8a, 8b and 8c and is connected to the output of the spectrometer 14 so as to read a signal supplied by each light receiver 12. In particular, the optical mixer 13 has a plurality of inputs, each connected to the light receiver 12 of a respective one of the optical sensors 8a, 8b and 8c, and an output connected to the input of the spectrometer 14.

The light receiver 12 of each optical sensor 8a, 8b, 8c is provided with an optical fibre designed to convey the light received by the light receiver 12 towards the optical mixer 13.

The spectrometer 14 is a known device capable of providing a distribution of the light intensity as the wavelength of the light radiation it receives as the input varies, i.e., it can measure the light radiation intensity of the various wavelengths that compose it. In particular, the spectrometer 14 divides the light radiation spectrum into a plurality of very narrow wavelength bands centred in respective wavelengths and returns a plurality of signals, each of which is indicative of the light intensity corresponding to a certain wavelength band. For simplicity, each signal provided by the spectrometer 14 will be considered below as corresponding to a certain wavelength, i.e., each of the aforementioned wavelength bands will be identified by the respective centre-band wavelength.

The control unit 17 is configured to activate the light emitter 11 of one optical sensor 8a, 8b, 8c at a time, leaving the other light emitters 11 disabled, and to read the signal supplied by the respective light receiver 12 so as to measure parameters of the organic fluids in one point of the blood circuit 2 at a time, that is, where the optical sensor 8a, 8b, 8c is. In other words, the optical sensor 8a alone, the optical sensor 8b alone, or the optical sensor 8c alone is used.

Preferably, the switching frequency of the measuring system 7, i.e., the frequency with which the acquisition system 9 sequentially turns on and off the light emitters 11 of the plurality of optical sensors 8a, 8b and 8c, is sufficiently low to allow the reading of a given optical sensor 8a, 8b, 8c by the control unit 17 to be completed before turning off the corresponding light emitter 11 and passing to that of the subsequent optical sensor 8a, 8b, 8c.

It is understood that the blood circuit 2 of the machine 1 may have a greater or lesser number of optical sensors than those shown in FIGS. 1-3, accordingly increasing or decreasing the number of measurement points within the blood circuit 2.

Preferably, the light emitter 11 of each optical sensor 8a, 8b, 8c is configured to emit white light, i.e., light with wavelengths throughout the visible light spectrum. In other words, the light emitter 11 emits electromagnetic radiation having a plurality of wavelengths distributed throughout the visible light spectrum. The spectrometer 14 is of the type suitable for operating throughout the visible light spectrum. As previously mentioned, the spectrometer 14 provides a plurality of output signals, each of which corresponds to the light intensity in a corresponding wavelength.

Lastly, the control unit 17 implements a plurality of Machine Learning algorithms, each designed to receive, as an input, all the signals coming from the spectrometer 14 and to combine them so as to determine a value of a respective parameter of the organic fluid flowing in the duct 5a, 5b, 5c associated with the optical sensor 8a, 8b, 8c.

In other words, the control unit 17 implements a plurality of Machine Learning algorithms specially developed and calibrated by means of a substantially known training process based on a series of measurements with a known result carried out by the optical sensors 8a-8c, so that a desired intrinsic parameter of the organic fluid flowing in the duct 5a, 5b, 5c can be measured based on the plurality of output signals provided by the spectrometer 14. In particular, each Machine Learning algorithm is associated with a parameter of an organic fluid to be measured with a given optical sensor 8a, 8b, 8c in a given duct 5a, 5b, 5c flown through by that organic fluid, and the training process consists in performing, through that optical sensor 8a, 8b, 8c, a large number of measurements, for example at least one hundred measurements, which provide predetermined values of the parameter, and calibrating the Machine Learning algorithm so that the control unit 7 provides these predetermined values.

Preferably, each Machine Learning algorithm implemented in the control unit 17 comprises at least one artificial neural network 18, i.e., a mathematical model consisting of a plurality of nodes interconnected at one or more levels, which receives as an input a plurality of values, and outputs a combination of all input values received. In greater detail, each neural network 18 comprises a linear combiner which adds up a plurality of contributions obtained from the multiplication of the signals coming out of the spectrometer 14 and respective weights previously obtained through an initial process of training of the neural network 18, based on a series of measurements with a known result.

A neural network has the technical advantage that it can be used to simulate complex relationships between inputs and outputs, which cannot be represented by analytical functions.

According to further embodiments of the control unit 17, the Machine Learning algorithms, for example, are statistical computational methods or adaptive data filtering methods.

With reference to the embodiment in FIG. 1, the control unit 17 is configured to measure the volume percentage of plasma extracted by means of the plasmafilter 3 relative to the blood taken from the patient, as a function of the signals provided by the optical sensors 8a and 8b. In other words, the control unit 17 is configured to implement a Machine Learning algorithm specially trained to calculate the difference in blood density due to the plasma extraction carried out by the pump 15c based on the output signals provided by the spectrometer 14 when the light emitters 11 of the optical sensors 8a and 8b are on.

With reference to the embodiment in FIG. 1, the control unit 17 is configured to measure a haemoglobin concentration in the plasma upstream of the fractionator filter 4, i.e., in the organic fluid inside the duct 5c, as a function of the signal provided by the optical sensor 8c. The control unit 17 is further configured to check whether the haemoglobin concentration measured in the plasma upstream of the fractionator filter 4 is higher than a predetermined threshold value, for example 1.5%.

Haemoglobin measured values higher than the aforementioned exemplary threshold value are indicative of the presence of haemoglobin in the plasma upstream of the fractionator filter 4, which in turn means that hemolysis is probably occurring, i.e., a red blood cell dissolution process with haemoglobin leakage. In other words, the control unit 17 is configured to implement a Machine Learning algorithm specially trained to check for the presence of hemolysis in the blood circuit 2 based on the output signals provided by the spectrometer 14 when the light emitter 11 of the optical sensor 8c is on.

With reference to the embodiment in FIG. 1, the control unit 17 is configured to measure the quantity of platelets in the plasma upstream of the fractionator filter 4, i.e., in the organic fluid inside the duct 5c, as a function of a signal provided by the optical sensor 8c. In other words, the control unit 17 is configured to implement a Machine Learning algorithm 18 specially trained to measure the quantity of platelets in the organic fluid inside the duct 5c, based on the output signals provided by the spectrometer 14 when the light emitter 11 of the optical sensor 8c is on.

The patient's blood filtration treatment ends with a phase of return of the blood contained in the plasmafilter 3 to the patient. To carry out the blood return phase, the duct 5a is removed from the patient's corresponding venous access and connected to a saline solution sac (not shown), the pump 15c remains turned off and the pump 15a is activated to feed the saline solution to the plasmafilter 3 so that the blood comes out of the plasmafilter 3 and returns to the patient through the duct 5b. However, the pump 15a must be stopped when all the blood has come out of the plasmafilter 3 and before the saline solution enters the patient's venous access.

In order to automatically manage the phase of return of the blood to the patient, the control unit 17 is configured to measure the volume percentage of blood flowing out of the plasmafilter 3 relative to the saline solution flowing into the plasmafilter 3, as a function of the signals provided by the optical sensors 8a and 8b, and to generate a pump 15a stopping event when the volume percentage of blood relative to the saline solution falls below a predetermined threshold value, for example 10%. In other words, the control unit 17 is configured to implement a Machine Learning algorithm specially trained to generate a pump 15a stopping event when the volume percentage of blood relative to the saline solution, as measured based on the output signals provided by the spectrometer 14 when the light emitters 11 of the optical sensors 8a and 8b are on, falls below a predetermined threshold value.

With reference now to the embodiment in FIG. 2, the control unit 17 is configured to measure, in a first instant, the hematocrit in the blood upstream of the dialyzer filter 23, i.e., in the organic fluid inside the duct 5a, as a function of a signal provided by the optical sensor 8a, to measure, in a second instant other than, and in particular after, the first instant, the hematocrit in the blood downstream of the dialyzer filter 23, i.e., in the organic fluid inside the duct 5b, as a function of a signal provided by the optical sensor 8b, to determine a hematocrit reduction as a function of the hematocrit measured in the first instant and in the second instant, and to determine the volume of liquid subtracted by the dialyzer filter 23, i.e., the patient's weight loss during the hemodialysis treatment, as a function of the hematocrit reduction. The time distance between said first and second instants is at least equal to the time it takes the blood to pass through the dialyzer filter 23, this time being a few seconds.

It is noted that the measuring system 7 is also suitable to be mounted on any other type of machine or apparatus for measuring parameters of other organic fluids, for example, dialysis fluid, fresh plasma or urine. For this purpose, the measuring system 7 comprises one or more optical sensors 8a-8c according to the type of machine or apparatus on which it is mounted.

According to a further embodiment, not shown, of the measuring system 7, the latter comprises a single optical sensor 8a, the acquisition system 9 is devoid of the optical mixer 13, and the light receiver 12 is directly connected to the input of the spectrometer 14.

The measuring system 1 and the corresponding blood filtering machine 1 described above have numerous advantages.

In the first place, the measuring system 7 is simpler and cheaper if compared to a known type of measuring system, in which each light emitter operates with a specific wavelength and not with broad spectrum light (i.e., white light), like the light emitter 11. In other words, the measuring system 7 has only one type of optical sensor (i.e., a white light sensor) that can be used for measuring any parameter, and the spectrometer 14 operating in the visible spectrum is cheaper than other spectrometers operating in other wavelengths, for example, the infrared range.

Secondly, the quality of the measurements obtained with the measuring system 7 does not depend on the quality of the reading window 10, and therefore a greater opacity of the reading window or of the material of the duct 5a, 5b, 5c does not deteriorate the quality of the measurement performed.

Furthermore, the combined use of the white light optical sensors with the Machine Learning algorithms implemented in the control unit 17 allows reproducible measurements of even very small values of the parameter of interest, for which the technology of the prior art is not able to provide reliable measurements. In fact, the use of white light increases the information available for training Machine Learning algorithms. This allows the measuring system 7 to detect small amounts of blood in the ducts of the blood circuit 2, thus allowing further possible uses of the system such as, for example, the checking for breaks in the blood circuit 2.

In addition, the measuring system 7 of the blood filtering machine 1 described above can be provided with a very large number of optical sensors, even though it comprises a single acquisition system 9, i.e., a single spectrometer 14 and a single control unit 17, since the optical sensors are of the same type.

It is therefore possible to measure several parameters in the same measurement point, thanks to the white light optical sensors, and/or to measure the same parameter in several measurement points within the blood circuit 2, without however increasing the cost of the measuring system 7.

Lastly, the measuring system 7 can be used in any circuit comprising ducts made of a transparent material in which organic fluids flow, to measure physical parameters of such organic fluids. For this purpose, it is sufficient to properly train the Machine Learning algorithms implemented in the control unit 17.

The invention claimed is:

1. A blood filtering machine comprising a blood circuit (2), which comprises at least one filter (3, 4; 23) and a plurality of ducts (5a-5c) made of a transparent material and designed to be flown through by organic fluids, and a measuring system (7) comprising: at least one optical sensor (8a-8c), which comprises a reading window (10) placed in a point of a respective duct of the plurality of ducts (5a-5c) so as to allow for the vision of the organic fluid flowing in the duct (5a-5c), a light emitter (11) to emit light towards the duct (5a-5c) through the reading window (10) and a light receiver (12) to receive said light after it has gone through the duct (5a-5c); and signal acquiring and processing means (9) to read a signal provided by the light receiver (12) and to measure at least one intrinsic parameter of the organic fluid in the duct (5a-5c) as a function of said signal; the machine (1) being characterized in that said at least one optical sensor comprises a plurality of optical sensors (8a-8c), each arranged on a respective duct of the plurality of ducts (5a-5c), and in that said signal acquiring and processing means (9) comprise one single spectrometer (14), an optical mixer (13), which comprises a plurality of inputs, each connected to the light receiver (12) of a respective one of the optical sensors (8a-8c), and an output connected to an input of the spectrometer (14), and a control unit (17), which is configured to activate the light emitter (11) of one optical sensor (8a-8c) at a time so as to measure a parameter of one organic fluid at a time.

2. The machine according to claim 1, wherein said at least one filter (3, 4) comprises a plasmafilter (3) designed to separate blood taken from a patient into plasma and corpuscular part and said plurality of ducts (5a-5c) comprises a first duct (5a) to convey blood taken from a patient to the plasmafilter (3) and said plurality of optical sensors (8a-8c) comprises a first optical sensor (8a) placed in a point of the first duct (5a).

3. The machine according to claim 1, wherein said at least one filter (3, 4) comprises a plasmafilter (3) designed to separate blood taken from a patient into plasma and corpuscular part and said plurality of ducts (5a-5c) comprises a second duct (5b) to receive said corpuscular part from the plasmafilter (3) and said plurality of optical sensors (8a-8c) comprises a second optical sensor (8b) placed in a point of the second duct (5b).

4. The machine according to claim 2, wherein said plurality of ducts (5a-5c) comprises a second duct (5b) to receive said corpuscular part from the plasmafilter (3), said plurality of optical sensors (8a-8c) comprises a second optical sensor (8b) placed in a point of the second duct (5b) and the control unit (17) is configured to measure a volume percentage of plasma extracted by means of said plasmafilter (3) relative to the blood taken from the patient, as a function of signals provided by the first optical sensor (8a) and by the second optical sensor (8b).

5. The machine according to claim 2, wherein said plurality of ducts (5a-5c) comprises a second duct (5b) to receive said corpuscular part from the plasmafilter (3), said plurality of optical sensors (8a-8c) comprises a second optical sensor (8b) placed in a point of the second duct (5b), said first duct (5a) is connectable to a saline solution container during a phase of return of the blood to the patient and the control unit (17) is configured to measure, during the phase of return of the blood to the patient, a volume percentage of blood flowing out of the plasmafilter (3) relative to the saline solution flowing into the plasmafilter (3), as a function of the signals provided by the first optical sensor (8a) and by the second optical sensor (8b), and to generate a blood return stopping event when the volume percentage of blood relative to the saline solution is below a predetermined threshold value.

6. The machine according to claim 1, wherein said at least one filter (3, 4) comprises a plasmafilter (3) designed to separate blood taken from a patient into plasma and corpuscular part, and a fractionator filter (4) designed to separate the plasma into a high molecular weight part and a low molecular weight part, said plurality of ducts (5a-5c) comprises a third duct (5c) to convey the plasma from the plasmafilter (3) to the fractionator filter (4) and said plurality of optical sensors (8a-8c) comprises a third optical sensor (8c) placed in a point of the third duct (5c).

7. The machine according to claim 6, wherein the control unit (17) is configured to measure a concentration of haemoglobin in the plasma upstream of said fractionator filter (4) as a function of a signal provided by said third optical sensor (8c).

8. The machine according to claim 6, wherein the control unit (17) is configured to measure a quantity of platelets of the organic fluid upstream of said fractionator filter (4) as a function of a signal provided by said third optical sensor (8c).

9. The machine according to claim 1, wherein said at least one filter comprises a dialyzer filter (23), said plurality of ducts (5a-5c) comprises a first duct (5a) to convey blood taken from a patient to the dialyzer filter (23) and a second duct (5b) to convey the blood treated by the dialyzer filter (23) to the patient and said plurality of optical sensors (8a-8c) comprises a first optical sensor (8a) placed in a point of the first duct (5a) and a second optical sensor (8b) placed in a point of the second duct (5b).

10. The machine according to claim 9, wherein the control unit (17) is configured to measure, in a first instant, the hematocrit in the blood upstream of the dialyzer filter (23) as a function of a signal provided by the first optical sensor (8a), to measure, in a second instant other than the first instant, the hematocrit in the blood downstream of the dialyzer filter (23) as a function of a signal provided by the second optical sensor (8b), to determine a hematocrit reduction as a function of the hematocrit measured in the first instant and in the second instant, and to determine a volume of liquid subtracted by the dialyzer filter (23) as a function of said hematocrit reduction.

11. The machine according to claim 1, wherein said light emitter (11) is configured to emit a white light and the spectrometer (14) operates in the entire visible light spectrum.

12. The machine according to claim 1, wherein said spectrometer (14) is configured to provide a plurality of output signals, each corresponding to the light intensity in a corresponding wavelength, and said control unit (17) is configured to implement a plurality of Machine Learning algorithms (18), each designed to receive, as an input, all the output signals of the spectrometer (14) and to combine them so as to determine the value of a corresponding parameter of an organic fluid in a given duct (5a-5c).

13. The machine according to claim 12, wherein each Machine Learning algorithm comprises an artificial neural network (18) trained based on a series of measures with a known result.

14. The machine according to claim 13, wherein each artificial neural network (18) comprises a linear combiner designed to add a plurality of contributions obtained from the multiplication of the signals coming out of the spectrometer (14) and respective weights previously obtained through an initial process of training of the artificial neural network (18).

* * * * *